United States Patent
Honda et al.

(10) Patent No.: US 9,198,710 B2
(45) Date of Patent: *Dec. 1, 2015

(54) TREATMENT SYSTEM

(71) Applicant: OLYMPUS CORPORATION, Tokyo (JP)

(72) Inventors: Yoshitaka Honda, Hachioji (JP); Takashi Irisawa, Hachioji (JP); Sadayoshi Takami, Hachioji (JP); Toshifumi Katsuragi, Hachioji (JP); Kazue Tanaka, Hachioji (JP)

(73) Assignee: OLYMPUS CORPORATION, Tokyo (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/162,442

(22) Filed: Jan. 23, 2014

(65) Prior Publication Data
US 2014/0207132 A1 Jul. 24, 2014

Related U.S. Application Data

(63) Continuation of application No. PCT/JP2013/065941, filed on Jun. 10, 2013.

(60) Provisional application No. 61/660,285, filed on Jun. 15, 2012.

(51) Int. Cl.
*A61B 18/12* (2006.01)
*A61B 18/10* (2006.01)
(Continued)

(52) U.S. Cl.
CPC ............. *A61B 18/10* (2013.01); *A61B 18/082* (2013.01); *A61B 18/085* (2013.01);
(Continued)

(58) Field of Classification Search
CPC ............. A61B 18/085; A61B 18/1233; A61B 2018/00714; A61B 2018/00892
USPC .......................................... 606/29, 31, 38, 34
See application file for complete search history.

(56) References Cited

U.S. PATENT DOCUMENTS 4,744,359 A 5/1988 Hatta et al.
6,547,786 B1 4/2003 Goble
(Continued)

FOREIGN PATENT DOCUMENTS

EP 1 053 719 A1 11/2000
EP 2 353 532 A1 8/2011
(Continued)

OTHER PUBLICATIONS

International Search Report issued in International Application No. PCT/JP2013/065941 on Jul. 16, 2013 (with translation).
(Continued)

*Primary Examiner* — Michael Peffley
*Assistant Examiner* — Thomas Giuliani
(74) *Attorney, Agent, or Firm* — Oliff PLC

(57) ABSTRACT

A treatment system includes a treatment instrument that has a pair of freely openable/closable holding sections for applying thermal energy generated by a heat generation section to a living tissue LT held between the holding sections, a signal output section that supplies an alternating current drive signal to the heat generation section, a setting section that sets a target temperature of the heat generation section, a signal detection section that detects a current and a voltage of the drive signal, a control section that controls a temperature of the heat generation section by adjusting power of the drive signal, a signal extraction section that extracts a direct current component from the drive signal detected by the signal detection section and a fault detection section that detects a precursory phenomenon of a fault of the heat generation section based on the extracted signal extracted by the signal extraction section.

8 Claims, 6 Drawing Sheets

(51) Int. Cl.
*A61B 18/08* (2006.01)
*A61B 18/00* (2006.01)

(52) U.S. Cl.
CPC *A61B 2018/0016* (2013.01); *A61B 2018/0063* (2013.01); *A61B 2018/00827* (2013.01); *A61B 2018/00892* (2013.01); *A61B 2018/00898* (2013.01)

(56) References Cited

U.S. PATENT DOCUMENTS

| | | | |
|---|---|---|---|
| 6,740,085 B2 * | 5/2004 | Hareyama et al. | 606/51 |
| 7,397,385 B1 | 7/2008 | Bajpay et al. | |
| 2006/0069388 A1 * | 3/2006 | Truckai et al. | 606/45 |
| 2007/0027653 A1 | 2/2007 | Godara | |
| 2007/0058304 A1 | 3/2007 | Parker et al. | |
| 2009/0157075 A1 * | 6/2009 | Wham et al. | 606/40 |
| 2010/0042097 A1 | 2/2010 | Newton et al. | |
| 2010/0145332 A1 | 6/2010 | Shibata et al. | |
| 2011/0037484 A1 * | 2/2011 | Gilbert | 324/649 |
| 2012/0022517 A1 | 1/2012 | Stuebe | |
| 2014/0214142 A1 * | 7/2014 | Honda et al. | 607/112 |
| 2014/0236140 A1 * | 8/2014 | Honda et al. | 606/34 |

FOREIGN PATENT DOCUMENTS

| | | |
|---|---|---|
| JP | B2-1-34618 | 7/1989 |
| JP | A-2000-350732 | 12/2000 |
| JP | 2006288430 A | 10/2006 |
| JP | B2-3911334 | 5/2007 |
| JP | 2009245978 A | 10/2009 |
| JP | B2-4653259 | 3/2011 |
| JP | A-2012-70779 | 4/2012 |
| WO | 9300862 A2 | 1/1993 |
| WO | WO 2010/064530 A1 | 6/2010 |

OTHER PUBLICATIONS

Jul. 24, 2015 Extended European Search Report issued in European Application No. 13804138.9.
Oct. 6, 2015 Extended European Search Report issued in Application No. 13 80 4265.

* cited by examiner

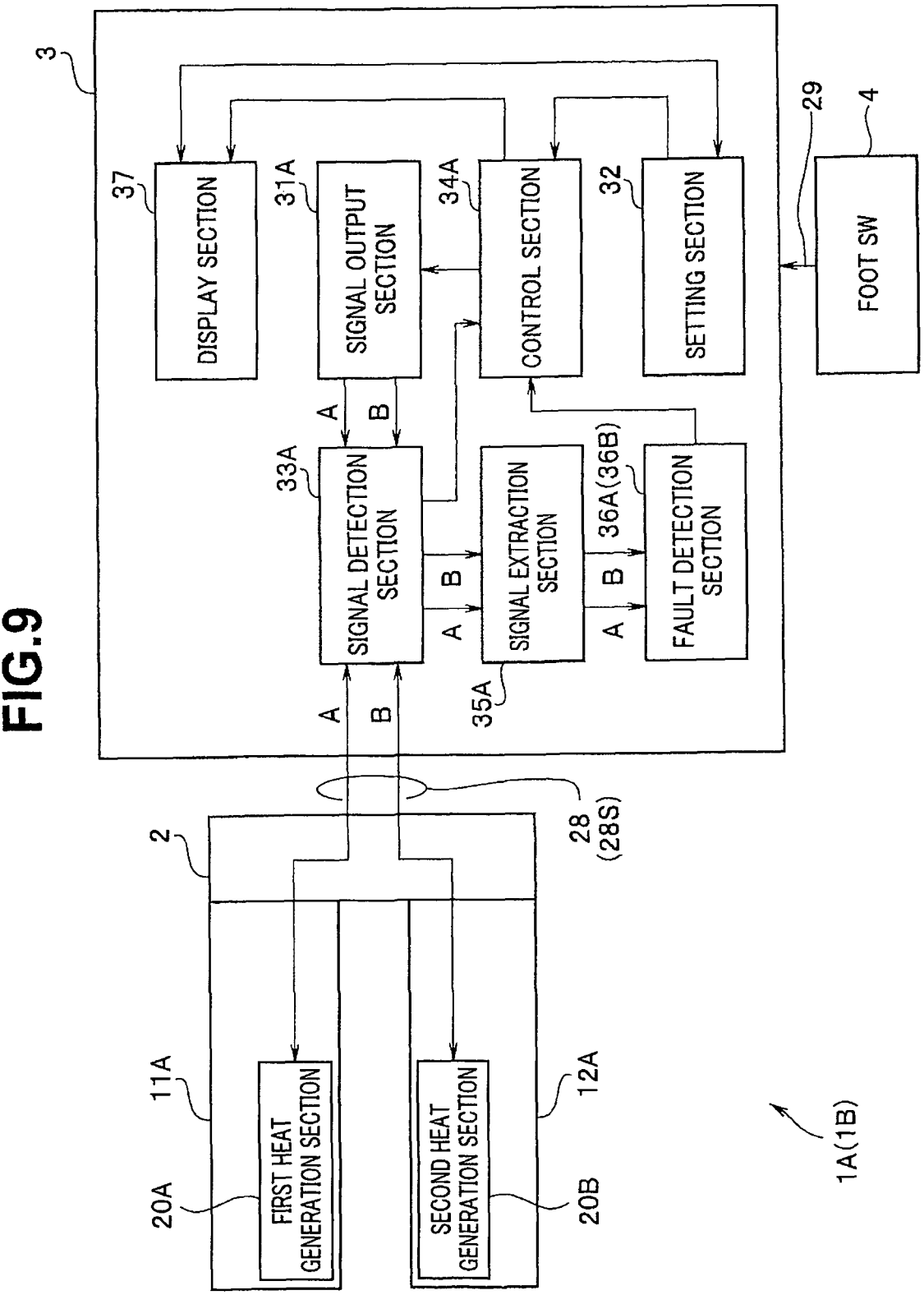

TREATMENT SYSTEM

CROSS REFERENCE TO RELATED APPLICATION

This application is a continuation application of PCT/JP2013/065941 filed on Jun. 10, 2013 and claims benefit of U.S. Provisional Patent Application No. 61/660,285 filed in the U.S.A. on Jun. 15, 2012, the entire contents of which are incorporated herein by this reference.

BACKGROUND OF THE INVENTION

1. Field of the Invention

The present invention relates to a treatment system that treats a living tissue held between a pair of holding sections by applying thermal energy thereto.

2. Description of the Related Art

Treatment systems are known which apply thermal energy to a living tissue held between a pair of holding sections of a treatment instrument. Such treatment systems coagulate or dissect a living tissue to be treated such as blood vessel.

Japanese Patent Application Laid-Open Publication No. 2012-70779 discloses a treatment system in which a pair of holding sections have a heat generation section and the heat generation section has a structure with a plurality of heat generating substrate portions including a thin film resistors connected via conductors. In this treatment system, the holding sections have a high degree of temperature uniformity and the holding sections can be easily downsized.

Here, although the treatment system is designed/manufactured so as to fully satisfy high-level reliability, faults are unavoidable. However, even when a fault occurs, if the fault position can be immediately identified, the treatment can be continued by replacing the faulty part by a spare part. For example, in the case where a fault is attributable to wire breakage of the heat generation section of the treatment instrument of the treatment system, the faulty treatment instrument may be replaced by a spare treatment instrument.

Japanese Patent No. 3911334 and Japanese Patent Publication No. 01-34618 disclose a treatment system that monitors resistance or the like of a heat generation section, judges a fault when the resistance falls outside a predetermined range and notifies a user of the fault.

SUMMARY OF THE INVENTION

A treatment system according to an embodiment includes a treatment instrument that has a first holding section including a first heat generation section and a second holding section including a second heat generation section, and applies thermal energy to a living tissue held between the first holding section and the second holding section, a signal output section that supplies alternating current drive signals respectively to the first heat generation section and the second heat generation section, a signal detection section that detects the drive signals, a signal extraction section that extracts direct current components respectively from the drive signals of the first heat generation section and the second heat generation section detected by the signal detection section as extracted signals, a fault detection section that detects a precursory phenomenon of a fault of the first heat generation section or the second heat generation section when either one of the extracted signals increases, and a control section that performs control, when the fault detection section detects the precursory phenomenon of the first heat generation section, so as to reduce power of the drive signal supplied to the first heat generation section and increase power of the drive signal supplied to the second heat generation section or performs control, when the fault detection section detects the precursory phenomenon of the second heat generation section, so as to reduce power of the drive signal supplied to the second heat generation section and increase power of the drive signal supplied to the first heat generation section.

A treatment system according to another embodiment includes a treatment instrument that has a first holding section including a first heat generation section and a second holding section including a second heat generation section, and applies thermal energy to a living tissue held between the first holding section and the second holding section, a signal output section that supplies alternating current drive signals respectively to the first heat generation section and the second heat generation section, a signal detection section that detects the drive signals, a signal extraction section that extracts direct current components respectively from the drive signals of the first heat generation section and the second heat generation section detected by the signal detection section as extracted signals, and a fault detection section that detects a precursory phenomenon of a fault of either one of the first heat generation section and the second heat generation section when a difference between the extracted signal extracted from the drive signal of the first heat generation section and the extracted signal extracted from the drive signal of the second heat generation section increases.

BRIEF DESCRIPTION OF THE DRAWINGS

FIG. 9 is a configuration diagram of a treatment system according to a second embodiment (third embodiment).

DETAILED DESCRIPTION OF THE PREFERRED EMBODIMENTS

First Embodiment

Hereinafter, a treatment system 1 according to a first embodiment of the present invention will be described with reference to the accompanying drawings.

Figure 1:
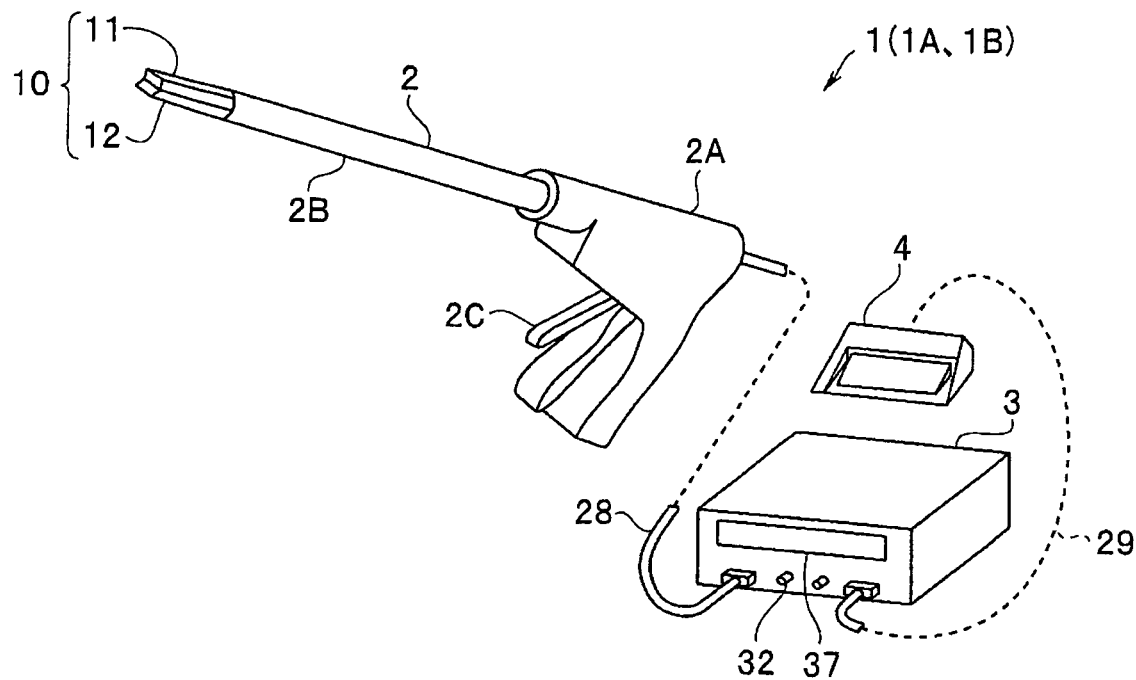
FIG. 1 is a perspective view illustrating an overall configuration of a treatment system according to a first embodiment.

As shown in FIG. 1, the treatment system 1 is provided with a treatment instrument 2, a main unit 3 and a foot switch 4. The treatment instrument 2 is a linear type instrument for surgery that performs treatment, for example, through an abdominal wall.

The treatment instrument 2 is provided with a grip 2A, a shaft 2B, and a pair of openable/closable holding sections 10 (a first holding section 11 and a second holding section 12) that hold and treat a living tissue LT to be treated. The grip 2A is connected to the main unit 3 via a cable 28. The grip 2A provided with an opening/closing knob 2C whereby an operator opens/closes the holding sections 10 has an easy-to grip shape, for example, an approximately L shape. The shaft 2B is disposed at an end of the grip 2A, which is integrated with the holding sections 10 to transmit operation of the opening/closing knob 2C to the holding sections 10. On the other hand, the other end of the grip 2A is a grasping portion grasped by the operator.

The main unit 3 has, on its front panel, a display section 37 that displays treatment conditions or the like and a setting section 32 for the operator to set the treatment conditions or the like, and the foot switch 4 is connected thereto via a cable 29. When the operator presses a pedal of the foot switch 4 with his/her foot, ON/OFF of a drive signal from the main unit 3 to the treatment instrument 2 is controlled. Note that the foot switch 4 is not an essential component, and the foot switch may be substituted by a switch or the like operated by the operator on his/her hand side.

Figure 2A:
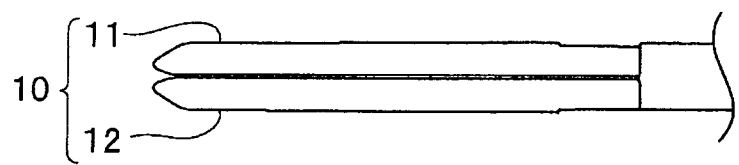
FIG. 2A is a side view of a pair of holding sections (closed state) of the treatment system of the first embodiment.
Figure 2B:
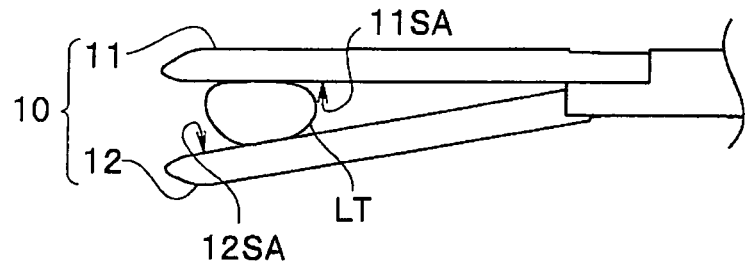
FIG. 2B is a side view of the treatment system of the first embodiment when the pair of holding sections hold a living tissue.
Figure 3A:
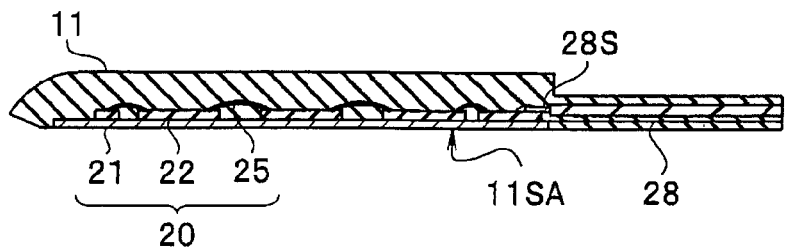
FIG. 3A is a diagram illustrating a cross-sectional structure in a major axis direction of a first holding section of the treatment system of the first embodiment.
Figure 3B:
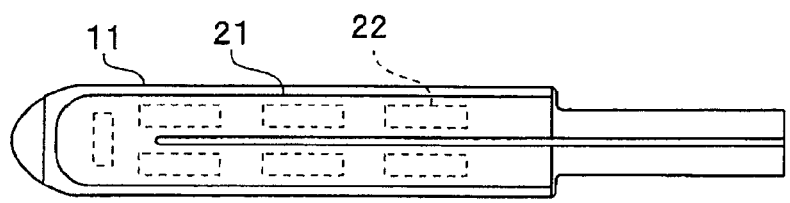
FIG. 3B is a top view of the first holding section of the treatment system of the first embodiment.
Figure 3C:
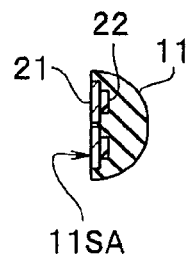
FIG. 3C is a diagram illustrating a cross-sectional structure in a short axis direction of the first holding section of the treatment system of the first embodiment.

As shown in FIG. 2A and FIG. 2B, the holding section 10 can be freely opened/closed when the second holding section 12 moves relative to the first holding section 11. That is, as shown in FIG. 2A, when the opening/closing knob 2C is not pressed by the operator, the second holding section 12 is proximate to or in contact with the first holding section 11 by an urging force of an elastic member (not shown). On the other hand, when the opening/closing knob 2C is pressed by the operator with a force stronger than the urging force of the elastic member as shown in FIG. 2B, the second holding section 12 detaches from the first holding section 11 and the holding section 10 is left open. While the holding section 10 is open, if the operator stops the operation of the opening/closing knob 2C, the living tissue LT inserted between the first holding section 11 and the second holding section 12 is held by being sandwiched and pressed between a holding surface 11SA of the first holding section 11 and a holding surface 12SA of the second holding section 12 by the urging force of the elastic member.

As shown in FIG. 3A to FIG. 4B, a heat generation section 20 that generates thermal energy is disposed on the holding surface 11SA of the first holding section 11. The heat generation section 20 is made up of a plurality of heat generating substrate portions 22 bonded to the back side (inner surface side) of a metal electrode substrate 21 which is, for example, a copper or SUS thin plate.

The heat generating substrate portion 22 is made of an insulator such as alumina or nitride aluminum, on a front side of which a thin film resistor 23 made of a metal such as platinum is formed. Platinum is a material having a positive temperature coefficient of resistance whose electric resistance R increases as its temperature rises. For this reason, it is possible to measure a temperature of the heat generation section 20 (thin film resistor 23) from the resistance R of the thin film resistor 23 as will be described later. The material of the thin film resistor 23 is not limited to platinum, and a high melting point metal material with various kinds of positive temperature coefficient of resistance such as NiCr alloy, Ta or W may also be used.

Figure 4A:
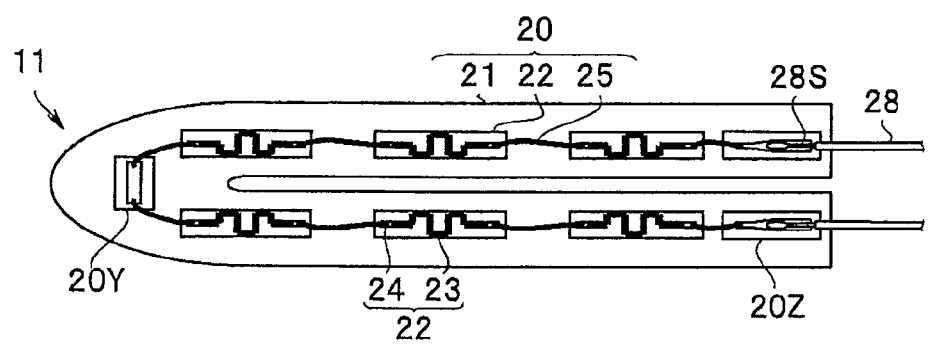
FIG. 4A is a top view illustrating a heat generation section of the first holding section of the treatment system of the first embodiment.
Figure 4B:
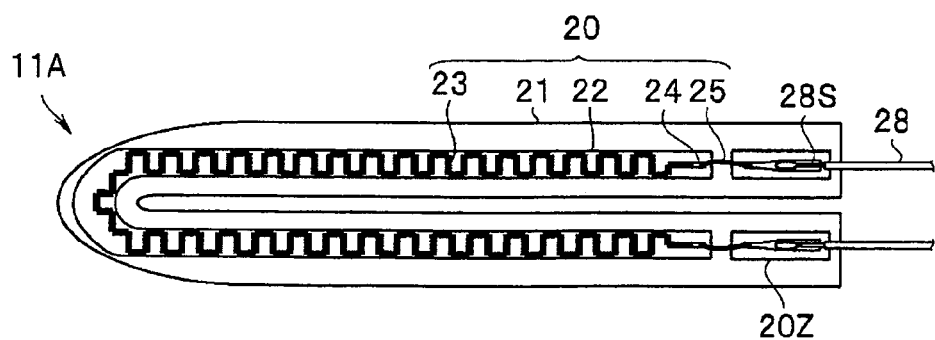
FIG. 4B is a top view illustrating the heat generation section of the first holding section of the treatment system of the first embodiment.

An electrode pad 24 made up of a multilayer film of, for example, Ti/Cu/Ni/Au is formed at an end of the thin film resistor 23. The thin film resistors 23 of the plurality of heat generating substrate portions 22 are connected in series via conductors 25 that connect the electrode pads 24 using, for example, a wire bonding technique. Note that as shown in FIG. 4A, a relay substrate portion 20Y may be disposed between the plurality of heat generating substrate portions 22. A connection substrate portion 20Z is disposed at the farthest end of the plurality of heat generating substrate portions 22 connected in series and a conductor 28S of a cable 28 is connected to the connection substrate portion 20Z.

Note that the plurality of heat generating substrate portions 22 of the heat generation section 20 may also be, for example, partially connected in parallel. Moreover, each heat generating substrate portion 22 may have a plurality of thin film resistors 23. Note that a heat generation section similar to that of the first holding section 11 may also be disposed on the second holding section 12 and the two heat generation sections may be connected in series or in parallel. Furthermore, as a first holding section 11A shown in FIG. 4B, an electrode pad 24 at an end of the continuous thin film resistors 23 may be connected to the connection substrate portion 20Z via a conductor 25.

A metal film (not shown) is formed on a main surface (back side) opposing a surface of the heat generating substrate portion 22 on which the thin film resistor is formed, and bonded to the metal electrode substrate 21 via, for example, a brazing metal having high thermal conductivity. For this reason, heat generated from the thin film resistor 23 is efficiently transferred to the metal electrode substrate 21 (holding surface 11SA).

Note that the surface of the first holding section 11 on which the thin film resistor is formed (front surface) is covered with an insulator such as polyimide and insulated. In order to prevent any adverse effect on living tissues surrounding the living tissue to be treated, the outer surface of the holding section 10 may be preferably made of a material having low thermal conductivity.

Figure 5:
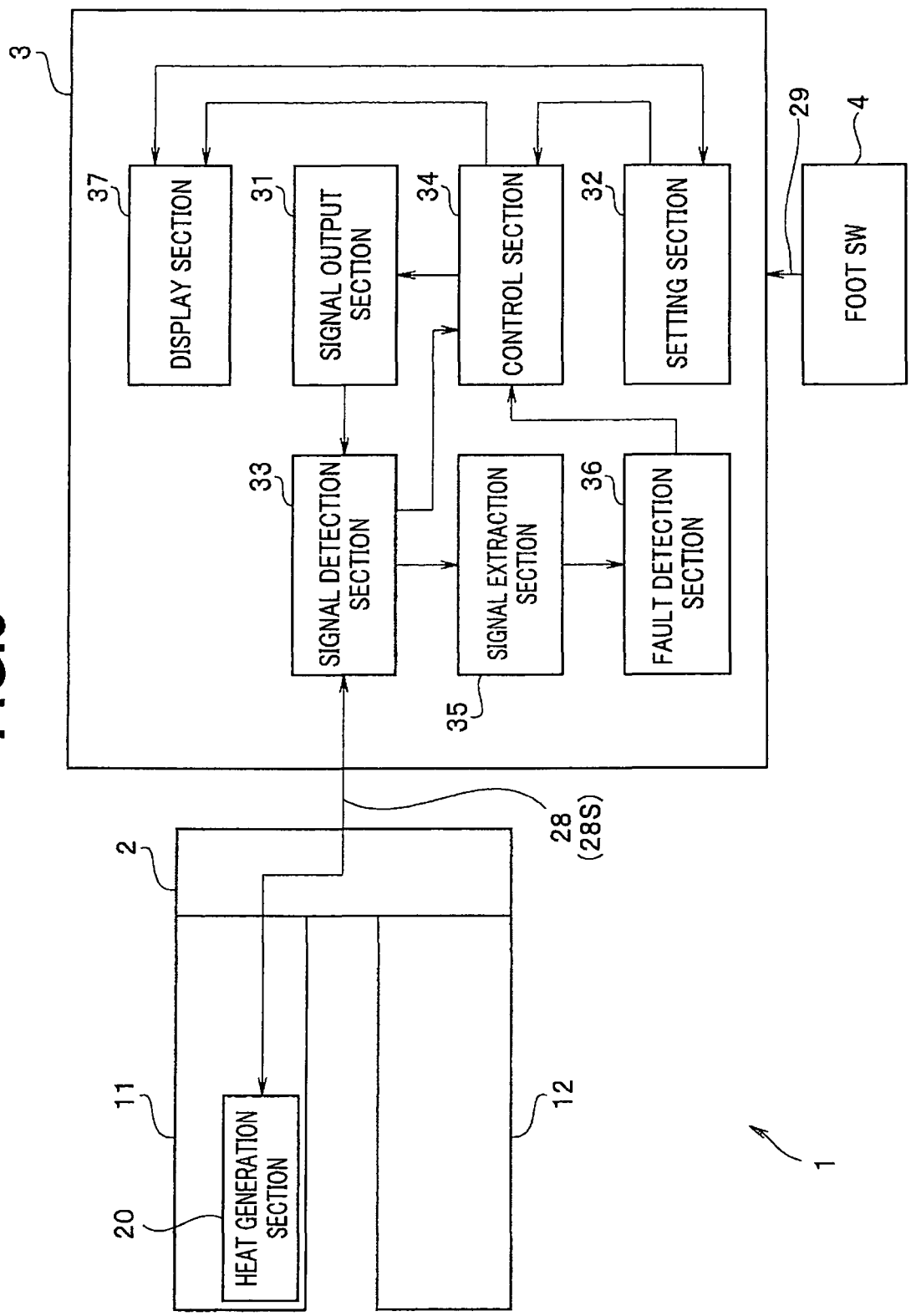
FIG. 5 is a configuration diagram of the treatment system of the first embodiment.

Next, the configuration of the treatment system 1 will be described using FIG. 5. As has already been described, the treatment system 1 has the treatment instrument 2, the main unit 3 and the foot switch 4.

The main unit 3 has a signal output section 31, a setting section 32, a signal detection section 33, a control section 34, a signal extraction section 35, a fault detection section 36, and a display section 37.

The signal output section 31 includes, for example, a high frequency signal oscillation section and an amplifier for supplying a drive signal, that is, heat generating power to the heat generation section 20. The setting section 32 is a switch, a mouse or a keyboard or the like used by the operator to set a target temperature T-set or the like of the heat generation section 20. The signal detection section 33 is a current sensor and a voltage sensor that detect a current I and a voltage V of a drive signal. Note that the signal detection section 33 may also be included in the treatment instrument 2. Moreover, for securing electrical safety, the alternating current drive signal outputted from the signal output section 31 is transmitted to the treatment instrument 2 via, for example, a pulse transformer. The control section 34 is a CPU or the like that controls a temperature of the heat generation section 20 by adjusting power of the drive signal (W=I×V). The signal extraction section 35 extracts a direct current component from the drive signal detected by the signal detection section 33. The fault detection section 36 detects a precursory phenomenon of a fault of the heat generation section 20 based on the extracted signal extracted from the signal extraction section 35.

Note that since the signal output section 31 and the signal detection section 33 process an analog signal, and the control section 34 processes a digital signal, the main unit 3 is provided with an AD conversion section (not shown).

As has already been described, the display section 37 displays a temperature of the heat generation section 20 during treatment, displays a temperature when the operator sets the target temperature T-set using the setting section 32, and also has a function of an announcement section that announces a warning as will be described later.

Note that the main unit 3 may have a high frequency signal output section. A high frequency signal outputted from the high frequency signal output section is applied to the pair of metal electrode substrates 21 of the treatment instrument 2. The operator can perform treatment on the living tissue LT held between the holding sections 10 using high frequency energy in addition to thermal energy. The signal output section having the function of the high frequency signal output section and the function of the signal output section 31 may alternately generate a high frequency signal and a drive signal for heat generation.

Figure 6:
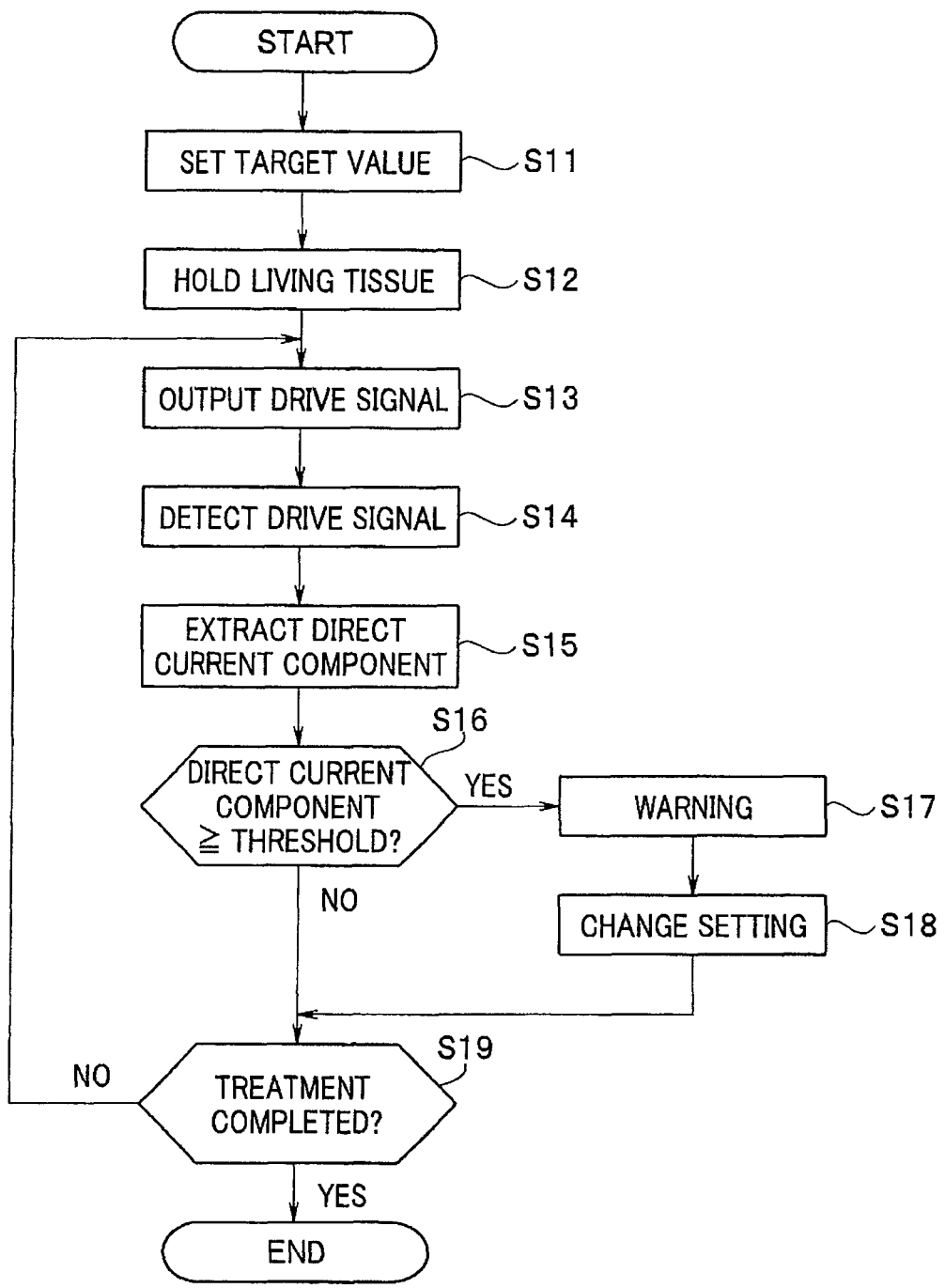
FIG. 6 is a flowchart illustrating a treatment flow of the treatment system of the first embodiment.

Next, operation of the treatment system 1 will be described with reference to the flowchart in FIG. 6.

<Step S11> Setting of Target Value

The operator sets a target temperature T-set of the heat generation section 20 which is a target value for treatment using the setting section 32. The target temperature T-set varies depending on the living tissue LT to be treated and may be, for example, 100° C. to 300° C. Note that at this time, a treatment end time t-end or the like may also be set. The treatment end time t-end is a treatment time period after the temperature becomes the target temperature T-set, for example. Note that the treatment end time t-end may be automatically set in accordance with an impedance or the like of the living tissue LT.

<Step S12> Holding of Living Tissue

As shown in FIG. 2A, the holding section 10 is in a closed state and is inserted, for example, into the abdominal cavity through the abdominal wall. When the operator performs pressing operation by grasping the opening/closing knob 2C of the grip 2A, the second holding section 12 is opened relative to the first holding section 11. The living tissue LT to be treated is then placed between the holding surface 11SA of the first holding section 11 and the holding surface 12SA of the second holding section 12. When the opening/closing knob 2C is released in this condition, the second holding section 12 is closed relative to the first holding section 11 by an urging force of the elastic member and the living tissue LT to be treated is held, pressed between the holding surface 11SA of the first holding section 11 and the holding surface 12SA of the second holding section 12.

<Step S13> Output of Drive Signal

While the living tissue LT is held between the pair of holding sections 10, the operator presses the foot switch 4 with his/her foot. The control section 34 then controls the signal output section 31 so as to output a drive signal. The drive signal is transmitted to the heat generation section 20 of the treatment instrument 2 via the cable 28. That is, the drive signal is applied to the thin film resistor 23 via the conductor 28S of the cable 28, the connection substrate portion 20Z of the heat generation section 20 and the conductor 25, and the thin film resistor 23 generates heat. The heat generated by the thin film resistor 23 is transferred to the living tissue LT via the heat generating substrate portion 22 and the metal electrode substrate 21.

<Step S14> Detection of Drive Signal

The signal detection section 33 detects a current I and a voltage V of the drive signal. As has already been described, since the thin film resistor 23 is made of a material having a positive temperature coefficient of resistance, when the temperature rises, the electric resistance R increases in proportion thereto. For this reason, it is possible to acquire the temperature of the heat generation section 20 by calculating the resistance R from the current I and the voltage V of the drive signal and using a prestored relationship expression between resistance and temperature. Of course, a temperature sensor may also be disposed in the heat generation section 20. However, it is possible to acquire the temperature of the heat generation section 20 in a simple configuration using the thin film resistor 23 made of a material having a positive temperature coefficient of resistance.

The control section 34 controls the signal output section 31 so that the temperature of the heat generation section 20 becomes the target temperature T-set and thereby adjusts power W of the drive signal, that is, the current I and the voltage V.

Figure 7:
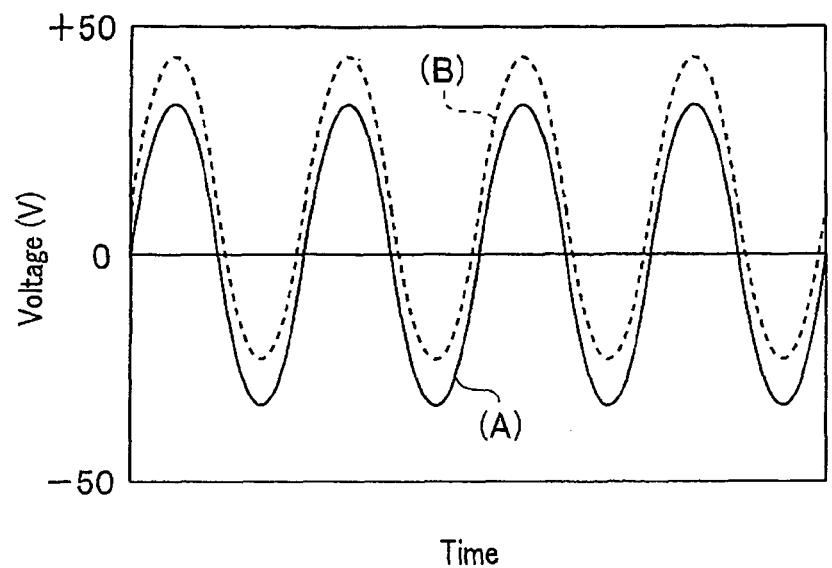
FIG. 7 is a diagram illustrating a drive signal of the treatment system of the first embodiment.

Since the drive signal outputted by the signal output section 31 is, for example, a high frequency sine wave alternating current signal, the drive signal (voltage) detected by the signal detection section 33 has the same peak voltage in a plus direction as that in a minus direction as shown in (A) of FIG. 7.

Figure 8:
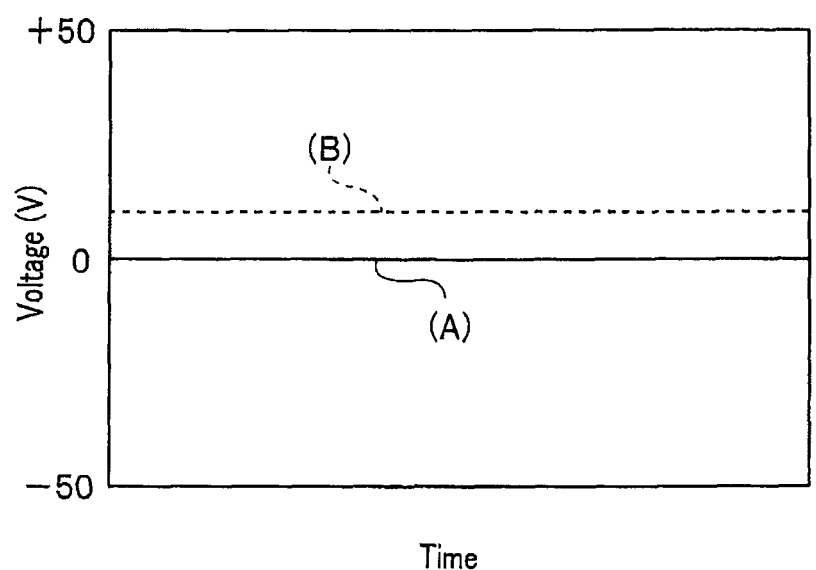
FIG. 8 is a diagram illustrating a direct current component of the drive signal of the treatment system of the first embodiment.

In contrast, as shown in FIG. 8, the present inventor discovered that a direct current component may be superimposed on the drive signal. Note that the treatment system 1 can perform normal treatment even when the drive signal changes as shown in FIG. 8. However, after the drive signal changes, drastically increasing/decreasing for a short period as shown in FIG. 8, if the treatment system 1 is continued to be used, the heat generation section 20 often malfunctions. For this reason, the occurrence of the drive signal change shown in FIG. 8 is called a "precursory phenomenon" of a fault.

In this precursory phenomenon, it is assumed that wire breakage has occurred in part of the circuit making up the heat generation section 20 and a discharge phenomenon (spark) has occurred between the ends of the broken wire.

When treatment was performed several to over ten times after the precursory phenomenon occurred, the probability that wire breakage would occur, causing a fault of the heat generation section 20 of the treatment instrument 2 was high.

<Step S15> Extraction of Signal

In the treatment system 1, the signal extraction section 35 extracts a direct current component (extracted signal) from the alternating current drive signal detected by the signal detection section 33. (A) in FIG. 8 shows an example of the extracted signal during normal operation and (B) shows an example of the extracted signal in the event of a precursory phenomenon.

The signal detection section 33 detects the current I and the voltage V of the drive signal, whereas the extraction target of the signal detection section 33 may be the current I or the voltage V. The extraction target may also be power (W) or resistance (R) calculated from the current I and the voltage V.

Note that although the detailed structure is different from the heat generation section 20 of the treatment system 1, in a treatment system having a heat generation section in which a thin film resistor is also connected via a conductor, it is possible to detect a precursory phenomenon of a fault (wire breakage) of the heat generation section 20 by extracting a direct current component as in the case of the treatment system 1. Thus, it has been confirmed that the precursory phenomenon is a common phenomenon among wire breakage faults in a heat generation section of a treatment system having the heat generation section in which thin film resistors are connected via a conductor.

<Step S16> Detection of Precursory Phenomenon

The fault detection section 36 detects a precursory phenomenon of a fault of the heat generation section 20 based on an extracted signal extracted by the signal extraction section 35. For example, when a maximum value of the extracted signal is equal to or above a predetermined threshold (S16: Yes), the fault detection section 36 assumes it as a precursory phenomenon of a fault of the heat generation section 20. For example, in the case shown in FIG. 8, the threshold voltage is set to on the order of 5 V.

Note that in the cases of the precursory phenomena shown in FIG. 7 and FIG. 8, a plus direct current voltage is applied as a bias, but a minus direct current voltage may also be applied. For this reason, the absolute value of the extracted signal is compared with a threshold voltage.

For example, the fault detection section 36 is made up of a reference voltage generation section that generates a predetermined threshold voltage and a comparator that compares the threshold voltage with the extracted signal, and outputs the comparison result to the control section 34 using, for example, a digital signal.

In order to detect a precursory phenomenon, the fault detection section 36 may also use an integral value of the extracted signal or a differential value of the extracted signal instead of a maximum value of the extracted signal.

<Step S17> Announcement of Warning

When the fault detection section 36 detects a precursory phenomenon (S16: Yes), the control section 34 controls the display section 37 which is an announcement section to display a warning. For the announcement of a warning, speech using a speaker (not shown) or the like may be used or an LED (not shown) or the like may be lit yellow. A warning may be announced after completing one treatment so as to prevent any confusion of the operator.

Note that the fault detection section 36 may not only detect a precursory phenomenon but also detect a fault of the heat generation section 20 from a drive signal. When a fault, that is, wire breakage occurs in the heat generation section 20, the electric resistance R increases significantly, and so it is easy to detect the fault. When the fault detection section 36 detects a fault, the control section 34 controls the display section 37 which is an announcement section so as to display a warning and also controls it so as to stop outputting a drive signal from the signal output section 31. Note that a warning may be announced by lighting an LED (not shown) or the like red.

<Step S18> Setting Change

Note that a time period from the occurrence of a precursory phenomenon to the occurrence of a fault may be very short. In this case, even if a precursory phenomenon is detected, a fault may occur before the treatment is completed and the treatment cannot be completed. For this reason, when the fault detection section 36 detects a precursory phenomenon (S16: YES), the control section 34 may perform control so as to reduce at least one of the target temperature T-set and power W of the drive signal.

For example, reducing the target temperature T-set extends the time period until the occurrence of a fault (wire breakage), and therefore the treatment can be completed. Note that when the target temperature T-set or power W is reduced, the treatment end time t-end may be preferably automatically extended so that predetermined thermal energy may be applied to the living tissue LT to be treated.

Note that step S18 is not an essential step for the treatment system 1.

<Step S19> Normal Control (Treatment Mode)

When the fault detection section 36 does not detect any precursory phenomenon (S16: No), the control section 34 performs normal control. That is, the control section 34 performs steps from step S13 until the treatment end time t-end elapses (S19: Yes), that is, the control section 34 controls the signal output section 31 so that the temperature of the heat generation section 20 becomes the target temperature T-set and adjusts power of the drive signal.

When the treatment end time t-end elapses (S19: Yes), the holding section 10 is extracted from within the abdominal cavity. Of course, when no precursory phenomenon is detected and the treatment is continued, the treatment from S11 or S12 is repeatedly done.

As described above, in the treatment system 1, the signal extraction section 35 extracts a direct current component from the drive signal detected by the signal detection section 33 and the fault detection section 36 detects a precursory phenomenon of a fault of the heat generation section 20 based on the extracted signal. For this reason, since the treatment instrument can be replaced by a spare treatment instrument after completion of the treatment, it is possible to prevent a fault from occurring in the middle of the treatment. Furthermore, when a setting change function is provided, it is further possible to reliably prevent the occurrence of a fault during the treatment by extending the time period until a fault occurs.

Thus, the treatment system 1 can speedily complete the treatment.

Second Embodiment

Next, a treatment system 1A of a second embodiment will be described. Since the treatment system 1A is similar to the treatment system 1, the same components are assigned the same reference numerals and description thereof will be omitted.

As shown in FIG. 9, in the treatment system 1A, a pair of holding sections (11A, 12A) of the treatment instrument 2 include heat generation sections 20A and 20B respectively. The first heat generation section 20A and the second heat generation section 20B are controlled independently. That is, a signal output section 31A outputs a drive signal A for driving the first heat generation section 20A and a drive signal B for driving the second heat generation section 20B. A signal detection section 33A detects a current and a voltage of the drive signal A and a current and a voltage of the drive signal B. A signal extraction section 35A extracts extracted signals (direct current components) A and B from drive signals A and B of the two heat generation sections 20A and 20B respectively. For this reason, a fault detection section 36A detects precursory phenomena of the two heat generation sections 20A and 20B independently.

A probability that the two heat generation sections 20A and 20B may simultaneously fail is not high. In the treatment system 1A, when the fault detection section 36A detects a precursory phenomenon of wire breakage of the first heat generation section 20A, a control section 34A reduces power of a drive signal supplied to the first heat generation section 20A and increases power of a drive signal supplied to the second heat generation section 20B. On the contrary, when the fault detection section 36A detects a precursory phenomenon of wire breakage of the second heat generation section 20B, the control section 34A reduces power of the drive signal supplied to the second heat generation section 20B and increases power of the drive signal supplied to the first heat generation section 20A.

In the treatment system 1 of the first embodiment, when a precursory phenomenon is detected, for example, the control section 34 performs control so as to reduce at least one of the target temperature T-set and power W of the drive signal, and it is therefore necessary to extend the treatment end time t-end so that predetermined thermal energy is applied to the living tissue LT to be treated.

In contrast, in the treatment system 1A, it is possible to apply predetermined thermal energy to the living tissue LT to be treated for a time period until the set treatment end time t-end while extending a time period from the detection of a precursory phenomenon to the occurrence of a fault (wire breakage).

Thus, the treatment system 1A has the effects of the treatment system 1 and can further speedily complete the treatment.

Third Embodiment

Next, a treatment system 1B according to a third embodiment will be described. Since the treatment system 1B is similar to the treatment system 1A or the like, the same components are assigned the same reference numerals and description thereof will be omitted.

In the treatment system 1B as in the case of the treatment system 1A, the pair of holding sections (11A, 12A) include the heat generation sections 20A and 20B respectively and the signal extraction section 35A extracts extracted signals (direct current components) A and B from drive signals of the two heat generation sections 20A and 20B.

In the treatment system 1B, a fault detection section 36B detects a precursory phenomenon based on a difference between the two extracted signals A and B.

That is, in the treatment system 1, the fault detection section 36 compares an extracted signal with a predetermined threshold and detects a precursor of a fault. However, a drive signal similar to a precursory phenomenon may be extracted depending on treatment conditions or the like.

As has already been described, a probability that the two heat generation sections 20A and 20B may simultaneously fail is not high. Since the treatment system 1B detects a precursory phenomenon based on a difference between the two extracted signals A and B, even if both of the two extracted signals A and B increase depending on treatment conditions or the like, the treatment system 1B will never mistake it for a precursory phenomenon.

The treatment system 1B has the effects of the treatment system 1 and further provides high accuracy of detecting a precursory phenomenon.

The present invention is not limited to the above-described embodiments, but various changes, alterations or the like may be made without departing from the spirit and scope of the present invention.

What is claimed is:

1. A treatment system comprising:
   a treatment instrument: (i) comprising: a first holding section including a first heat generation section, and a second holding section including a second heat generation section, and (ii) configured to apply thermal energy to a living tissue held between the first holding section and the second holding section;
   a signal output section configured to supply a first alternating current drive signal to the first heat generation section in order to heat the first heat generation section, and supply a second alternating current drive signal to the second heat generation section in order to heat the second heat generation section;
   a signal detection section configured to detect the first and second drive signals;
   a signal extraction section configured to extract a direct current component superimposed on the first drive signal as a first extracted signal on the basis of the first drive signal, and extract a direct current component superimposed on the second drive signal as a second extracted signal on the basis of the second drive signal;
   a fault detection section configured to: (1) detect the first extracted signal as a precursory phenomenon of a fault of the first heat generation section, when the first extracted signal exceeds a predetermined threshold, and (2) detect the second extracted signal as a precursory phenomenon of a fault of the second heat generation section, when the second extracted signal exceeds the predetermined threshold; and
   a control section configured to control the signal output section on the basis of a result of detection of the fault detection section, wherein
      (i) when the fault detection section detects the precursory phenomenon of the first heat generation section, the control section reduces the first drive signal supplied to the first heat generation section, and increases the second drive signal supplied to the second heat generation section, and
      (ii) when the fault detection section detects the precursory phenomenon of the second heat generation section, the control section reduces the second drive signal supplied to the second heat generation section, and increases the first drive signal supplied to the first heat generation section.

2. The treatment system according to claim 1, wherein each of the first extracted signal and the second extracted signal are voltage values.

3. The treatment system according to claim 1, wherein each of the first heat generation section and the second heat generation section comprise a heat generating substrate portion having a thin film resistor, the heat generating substrate portion being connected to a conductor.

4. The treatment system according to claim 1, further comprising an announcement section that announces a warning when the fault detection section detects the precursory phenomenon.

5. A treatment system comprising:
   a treatment instrument: (i) comprising: a first holding section including a first heat generation section, and a second holding section including a second heat generation section, and (ii) configured to apply thermal energy to a living tissue held between the first holding section and the second holding section;
   a signal output section configured to supply a first alternating current drive signal to the first heat generation section in order to heat the first heat generation section, and supply a second alternating current drive signal to the second heat generation section in order to heat the second heat generation section;

a signal detection section configured to detect the first and second drive signals supplied from the signal output section;

a signal extraction section configured to extract a direct current component superimposed on the first drive signal as a first extracted signal on the basis of the first drive signal detected by the signal detection section, and extract a direct current component superimposed on the second drive signal as a second extracted signal on the basis of the second drive signal detected by the signal detection section;

a fault detection section configured to: (1) detect a precursory phenomenon of a fault of the first heat generation section, and (2) detect a precursory phenomenon of a fault of the second heat generation section on the basis of a difference between the first extracted signal, and the second extracted signal extracted by the signal extraction section; and a control section configured to control the signal output section on the basis of a result of detection by the fault detection section, wherein (i) when the fault detection section detects the precursory phenomenon of the first heat generation section, the control section reduces the first drive signal supplied to the first heat generation section, and increases the second drive signal supplied to the second heat generation section, and (ii) when the fault detection section detects the precursory phenomenon of the second heat generation section, the control section reduces the second drive signal supplied to the second heat generation section, and increases the first drive signal supplied to the first heat generation section.

6. The treatment system according to claim 5, wherein each of the first heat generation section and the second heat generation section comprise a heat generating substrate portion having a thin film resistor, the heat generating substrate portion being connected to a conductor.

7. The treatment system according to claim 5, wherein each of the first extracted signal and the second extracted signal are voltage values.

8. The treatment system according to claim 5, further comprising an announcement section that announces a warning when the fault detection section detects the precursory phenomenon.

* * * * *